US00PP21863P2

(12) United States Plant Patent
Zaiger et al.

(10) Patent No.: US PP21,863 P2
(45) Date of Patent: Apr. 12, 2011

(54) INTERSPECIFIC TREE NAMED 'LEAH COT'

(50) Latin Name: ***Interspecific Prunus* species**
Varietal Denomination: Leah Cot

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 12/655,177

(22) Filed: Dec. 24, 2009

(51) Int. Cl.
*A01H 5/00* (2006.01)

(52) U.S. Cl. ..... Plt./180

(58) Field of Classification Search ..... Plt./180
See application file for complete search history.

*Primary Examiner* — Susan B McCormick Ewoldt

(57) ABSTRACT

A new and distinct variety of interspecific tree and its fruit are characterized with the tree budded on 'Nemagaurd' Rootstock (non-patented), grown on Handford sandy loam soil with Storie Index rating 95, in USDA Hardiness Zone 9, near Modesto, Calif. with Standard commercial fruit growing practices, such as pruning, thinning, spraying, irrigation and fertilization. Its novelty consist of the following combination of desirable features:

1. Fruit with an attractive orange skin color.
2. Fruit with very good flavor and eating quality.
3. Fruit with an average Brix of 18.0° and a good balance between acid and sugar.
4. Regular and productive bearer of fruit.
5. Vigorous, semi-spreading tree growth.

1 Drawing Sheet

Botanical classification: Interspecific *Prunus* species.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of apricot and interspecific trees, which are known to us, and mentioned herein, 'Cot-N-Candy' Interspecific (U.S. Plant Pat. No. 17,827) and the proprietary interspecific '42ZC692'.

STATEMENT REGARDING FEDERALLY SPONSORED RESEARCH AND DEVELOPMENT

Not applicable.

ORIGIN OF THE VARIETY

The new variety of interspecific tree, a combination of crosses between (*Prunus armeniaca* and *Prunus salicina*) was originated by us in our experimental orchard located near Modesto, Calif. from an open pollinated proprietary interspecific seedling selection with the identification number '42ZC692'. The seed parent (42ZC692) originated from an open pollinated seedling selection grown from the interspecific tree 'Cot-N-Candy' (U.S. Plant Pat. No. 17,827). A large number of these open pollinated seedlings were budded on established trees of 'Nemagaurd' Rootstock (non-patented) to enhance earlier fruit production and under close and careful observation the present seedling exhibited desirable fruit and tree characteristics and was selected in 2003 for asexual propagation and commercialization.

ASEXUAL REPRODUCTION OF THE VARIETY

Asexual reproduction of the new and distinct variety of interspecific tree was by budding to 'Nemagaurd' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of interspecific tree, [Apricot×((Plum×Plumcot)×Plumcot)×Apricot]×[unknown pollen] is of large size, vigorous, semi-spreading growth and a productive and regular bearer of large size, orange flesh, freestone fruit with very good flavor and eating quality. The fruit is further characterized by having firm flesh, an attractive orange skin color, being relatively uniform in size and maturity throughout the tree and having good handling, storage and shipping quality, with an average Brix of 18.0°. In comparison to the immediate interspecific parent (42ZC692), the fruit of the new variety has orange flesh and skin compared to yellow, is larger in size and is higher in soluble solids (Brix). In comparison to the interspecific 'Cot-N-Candy' (U.S. Plant Pat. No. 17,827), the new variety has orange flesh and skin compared to light whitish yellow and is higher in Brix.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 7 year old specimens grown near Modesto, Calif., with color in accordance with Munsell Book of Color.

Tree:

*Size.*—Large, usually pruned to 3 to 3.5 meters in height and width for economical harvesting of fruit, varies with different cultural practices.

*Vigor.*—Vigorous, tree growth of approximately 1.5 to 2 meters in height the first growing season. Varies with type and fertility of soil, climatic conditions and cultural practices.

*Form.*—Semi-spreading, usually pruned to vase shape.

*Branching habit.*—Semi-spreading, crotch angle approximately 40°, increases with heavy crop load.

*Productivity.*—Productive, thinning and spacing of fruit necessary for desired marketable size. Fruit set varies with climatic conditions during blooming period.

*Bearer.*—Regular, adequate fruit set 5 consecutive years. No alternate bearing observed.

*Fertility.*—Self fertile, sets fruit under bag.

*Density.*—Medium dense, pruned to vase shape to allow sunlight to center of tree to enhance fruit color and health of fruit spurs.

*Hardiness.*—Hardy in all stone fruit growing areas of California. Tree grown in USDA Hardiness Zone 9. Winter chilling requirement approximately 850 hours at or below 45° F.

Trunk:

*Size.*—Medium. Average circumference 49.8 cm at 25.4 cm above ground on a 7 year old tree.

*Stocky.*—Medium stocky.

*Texture.*—Medium shaggy, becomes rougher with age.

*Color.*—Varies from 7.5YR 2/2 to 10YR 4/2.

Branches:

*Size.*—Medium. Average circumference 14.3 cm at 1.2 meters above ground. Crotch angle approximately 40°, increases with heavy crop load.

*Surface texture.*—New growth smooth. Mature growth medium rough, becomes rougher with age.

*Lenticels.*—Size — medium. Average number 16 in a 25.8 sq cm area of branch. Average length 3.4 cm. Average width 1.4 cm. Color varies from 2.5Y 7/10 to 2.5Y 6/10.

*Color.*—New growth varies from 2.5YR 3/4 to 5GY 4/6. Old growth varies from 2.5YR 2/4 to 5YR 2/4, varies with age of growth.

Leaves:

*Size.*—Medium to large. Average length 97.4 mm. Average width 85.8 mm.

*Form.*—Ovate.

*Apex.*—Cuspidate.

*Base.*—Obtuse.

*Margin.*—Doubly serrate.

*Thickness.*—Medium.

*Surface texture.*—Upper surface relatively smooth, slightly indented over Midrib and leaf veins, glabrous. Lower surface relatively smooth, small ridges created by midrib and pinnate venation, glabrous.

*Petiole.*—Average length 43.5 mm. Average width 1.8 mm. Longitudinally grooved, very shallow. Surface — glabrous. Color varies from 7.5R 3/6 to 2.5GY 6/6, color varies with exposure to sunlight.

*Glands.*—Type — globose. Size — small. Average length 0.6 mm. Average diameter 0.3 mm. Number varies from 1 to 3, average number 2. Located primarily on upper portion of petiole and base of leaf blade. Color varies from 2.5GY 5/4 to 2.5GY 5/6.

*Stipules.*—None observed on mature leaves.

*Color.*—Upper surface varies from 5GY 3/6 to 7.5GY 3/4. Lower surface varies from 5GY 4/4 to 5GY 3/4. Midvein color varies from 2.5GY 7/6 to 5GY 7/6.

Flower buds:

*Size.*—Medium. Average length 14.7 mm. Average diameter 8.5 mm.

*Hardiness.*—Hardy in all stone fruit growing areas of California.

*Form.*—Conical, becoming slightly elongated before opening.

*Pedicel.*—Average length 1.9 mm. Average width 1.7 mm. Color varies from 2.5GY 7/6 to 5GY 8/6.

*Color.*—Varies from N9.5/ (white) to 7.5RP 5/12.

*Number of buds per spur.*—Average number 2, varies from 1 to 3.

Flowers:

*Blooming period.*—Date of First Bloom Feb. 25, 2009. Date of Petal Fall Mar. 8, 2009, varies slightly with climatic conditions.

*Size.*—Medium to large. Average height 17.7 mm. Average diameter 27.8 mm.

*Petals.*—Number 5, alternately arranged to sepals. Average length 15.2 mm. Average width 14.9 mm. Margin — entire. Both upper and lower surfaces glabrous. Shape — orbicular. Color varies from N9.5/ (white) to 7.5RP 5/10, fades with age of flower.

*Sepals.*—Normally 5, alternately arranged to petals. Shape — triangular. Margin — entire. Average length 6.7 mm. Average width 5.4 mm. Both upper and lower surfaces glabrous. Color — upper surface 5GY 8/4 to 2.5R 2/8. Lower surface 2.5R 2/6 to 5R 2/6.

*Stamens.*—Average number per flower 29. Average filament length 11.7 mm. Filament color N9.5/ (white). Anther color varies from 5Y 8.5/8 to 5Y 8/10.

*Pollen.*—Abundant. Self fertile, sets fruit under bag. Color varies from 5Y 8/10 to 5Y 7/10.

*Pistil.*—Number — normally one. Surface — pubescent. Average length 16.6 mm. Position of stigma to anthers — even. Color varies from 7.5Y 8.5/6 to 10Y 8/6.

*Fragrance.*—Moderate aroma.

*Color.*—Varies from N9.5/ (white) to 7.5RP 5/10, fades with age of flower.

*Number flowers per flower bud.*—Usually one, varies from 1 to 3.

*Pedicel.*—Average length 2.1 mm. Average width 1.8 mm. Color varies from 2.5GY 8/6 to 5GY 7/6.

Fruit:

*Maturity when described.*—Firm ripe.

*Date of first picking.*—Jun. 10, 2009.

*Date of last picking.*—Jun. 20, 2009, varies slightly with climatic conditions.

*Size.*—Medium. Average diameter axially 55.9 mm. Average transversely in suture plane 57.7 mm. Average across suture plane 53.4 mm. Average weight 90.9 grams, varies slightly with fertility of the soil, amount of thinning and climatic conditions.

*Form.*—Slightly elongated.

*Suture.*—Slightly lipped.

*Ventral surface.*—Shallow, extends from base to apex.

*Apex.*—Slightly retuse.

*Base.*—Varies from flat to slightly retuse.

*Stem cavity.*—Rounded to slightly elongated in suture plane. Average depth 3.0 mm. Average diameter 5.0 mm.

Stem:

*Size.*—Small. Average length 6.7 mm. Average diameter 3.4 mm.

*Color.*—Varies from 2.5GY 5/8 to 5GY 5/8.

Flesh:

*Ripens.*—Evenly.

*Texture.*—Firm, apricot texture, smooth and juicy.

*Fibers.*—Few, small, tender.

*Firmness.*—Firm, comparable to commercial apricots.

*Aroma.*—Moderate to heavy.

*Amydgalin.*—Undetected.

*Eating quality.*—Very good.

*Flavor.*—Very good, good balance between acid and sugar.

*Juice.*—Moderate amount, enhances flavor.

*Brix.*—Average Brix 18.0°, varies slightly with amount of fruit per tree and climatic conditions.

*Color.*—Varies from 6.25YR 6/12 to 6.25YR 7/14. Pit cavity varies from 6.25YR 7/14 to 8.75YR 7/12.

Skin:

*Thickness.*—Medium.

*Surface.*—Slightly waffled.

*Pubescence.*—Moderate pubescence, short in length.

*Tendency to crack.*—None.

*Color.*—Ground color varies from 6.25YR 7/12 to 6.25YR 6/12. Overspread with 6.25R 4/12.

*Tenacity.*—Tenacious to flesh.

*Astringency.*—None.

Stone:

*Type.*—Freestone.

*Size.*—Medium. Average length 24.2 mm. Average width 21.1 mm. Average thickness 14.3 mm.

*Form.*—Obovoid.

*Base.*—Flat.

*Apex.*—Slightly pointed. Average length 0.7 mm.

*Surface.*—Lightly pitted throughout, a shallow groove on each side of suture extending from base to apex.

*Sides.*—Unequal, one side extending further from suture plane.

*Ridges.*—Very narrow, a small ridge near groove on each side of suture.

*Tendency to split.*—None.

*Color.*—Varies from 10YR 4/4 to 2.5Y 3/4.

Kernel:

*Size.*—Medium. Average length 18.2 mm. Average width 13.1 mm. Average depth 9.2 mm.

*Form.*—Ovate.

*Viability.*—Viable, complete embryo development.

*Skin.*—Color varies from 5Y 9/2 to 7.5Y 9/2.

Use: Dessert. Market — local and long distance.

Keeping quality: Relatively good, held firm in cold storage 12 days at 38° to 42° F. without shriveling, internal breakdown of flesh or appreciable loss of eating quality.

Shipping quality: Good, showed minimal flesh bruising or skin scarring during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct interspecific tree, substantially as illustrated and described.

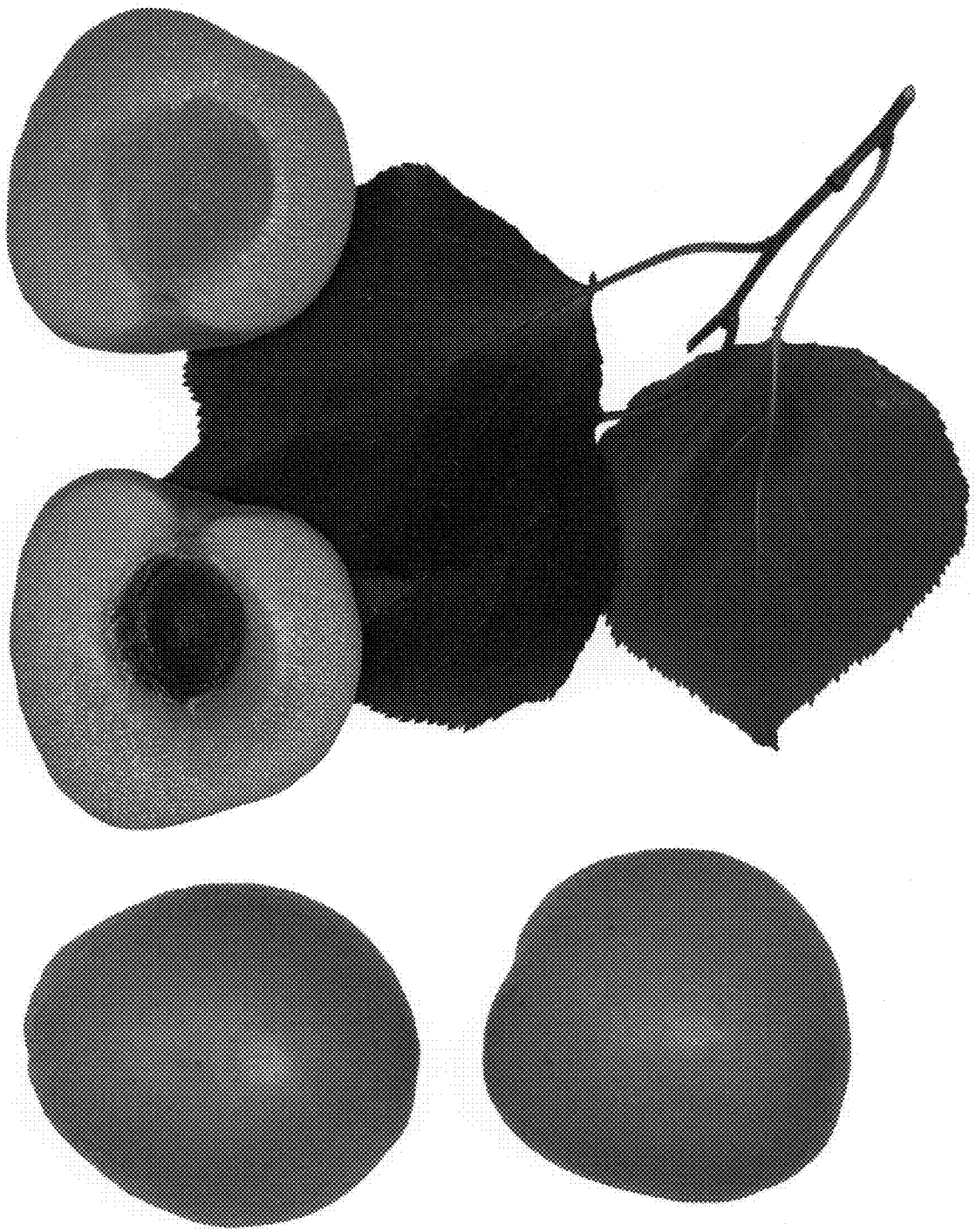

* * * * *